United States Patent
Bottom et al.

(10) Patent No.: US 11,898,646 B2
(45) Date of Patent: Feb. 13, 2024

(54) ADJUSTABLE VALVE

(71) Applicant: INTERSURGICAL AG, Vaduz (LI)

(72) Inventors: David Simon Bottom, Wokingham (GB); Christopher Edgerly Booth, Wokingham (GB); Simon Robert Payne, Wokingham (GB); Richard Francis Bowsher, Wokingham (GB)

(73) Assignee: INTERSURGICAL AG, Vaduz (LI)

( * ) Notice: Subject to any disclaimer, the term of this patent is extended or adjusted under 35 U.S.C. 154(b) by 0 days.

(21) Appl. No.: 17/621,811

(22) PCT Filed: Jun. 25, 2020

(86) PCT No.: PCT/EP2020/067950
§ 371 (c)(1),
(2) Date: Dec. 22, 2021

(87) PCT Pub. No.: WO2020/260536
PCT Pub. Date: Dec. 30, 2020

(65) Prior Publication Data
US 2022/0260166 A1    Aug. 18, 2022

(30) Foreign Application Priority Data
Jun. 25, 2019 (GB) .................... 1909121

(51) Int. Cl.
*F16K 17/06* (2006.01)
*A61M 16/20* (2006.01)
(Continued)

(52) U.S. Cl.
CPC ........ *F16K 17/06* (2013.01); *A61M 16/206* (2014.02); *F16K 27/0209* (2013.01); *F16K 15/063* (2013.01); *Y10T 137/7929* (2015.04)

(58) Field of Classification Search
CPC ........ Y10T 137/7929; Y10T 137/7876; F16K 17/06
(Continued)

(56) References Cited

U.S. PATENT DOCUMENTS 347,213 A * 8/1886 Walker .................... F16K 17/06
                                                        137/540
401,391 A * 4/1889 Stuck ...................... F16K 17/06
                                                        425/173
(Continued)

FOREIGN PATENT DOCUMENTS

EP       1228781 A2    8/2002
EP     1 886 706 A1    2/2008
(Continued)

OTHER PUBLICATIONS

International Search Report and Written Opinion for corresponding Application No. PCT/EP2020/067950 (dated Oct. 5, 2020).
(Continued)

*Primary Examiner* — Robert K Arundale
(74) *Attorney, Agent, or Firm* — Troutman Pepper Hamilton Sanders LLP (Rochester)

(57) ABSTRACT

The present invention relates to adjustable flow control valves, for example to an Adjustable Pressure Limiting (APL) valve. The adjustable valve (2) described comprises a valve body (4) comprising a valve seat (6), a valve member (10) movable relative to the valve seat (6), a first valve cap (20), a second valve cap (50) and a biasing element (30) to bias the valve member (10) away from the first valve cap (20). The first valve cap (20) is movable to increase the biasing force applied by the biasing element (30). The second valve cap (50) is engageable with the first valve cap (20) to prevent such movement of the first valve cap (20) beyond a selected position, but to allow movement of the
(Continued)

first valve cap (20) in an opposite direction, way from said position.

19 Claims, 6 Drawing Sheets

(51) Int. Cl.
*F16K 27/02* (2006.01)
*F16K 15/06* (2006.01)
(58) Field of Classification Search
USPC ................................................ 251/93, 186
See application file for complete search history.

(56) References Cited

U.S. PATENT DOCUMENTS

| | | | | |
|---|---|---|---|---|
| 427,264 | A * | 5/1890 | Iwanowitsch | F16K 17/168 137/540 |
| 1,187,300 | A * | 6/1916 | Girard et al. | B60S 5/043 137/227 |
| 1,482,517 | A * | 2/1924 | Kelsey | B60C 23/0496 137/227 |
| 1,743,350 | A * | 1/1930 | Hopkins | F16K 17/06 411/374 |
| 2,254,209 | A | 9/1941 | Buttner et al. | |
| 2,353,306 | A * | 7/1944 | Henry | F16K 17/06 137/542 |
| 2,412,205 | A * | 12/1946 | Cook | B63C 7/12 114/54 |
| 2,601,563 | A * | 6/1952 | Selwyn | F16K 17/0433 251/336 |
| 2,683,464 | A * | 7/1954 | St Clair | F16K 17/0466 137/540 |
| 2,908,288 | A * | 10/1959 | Carr | F16K 17/06 137/540 |
| 3,422,840 | A | 1/1969 | Bryant et al. | |
| 3,796,228 | A * | 3/1974 | Bedo | F16K 17/04 137/543.13 |
| 4,103,704 | A * | 8/1978 | Richards | F16K 17/06 137/522 |
| 4,312,376 | A * | 1/1982 | Allen | F16K 15/063 251/282 |
| 4,530,373 | A * | 7/1985 | Bork, Jr. | F16K 17/04 137/538 |
| 4,727,902 | A * | 3/1988 | Unterstein | F02K 9/38 137/540 |
| 4,790,348 | A * | 12/1988 | Gausman | F16K 17/04 251/86 |
| 5,294,093 | A | 3/1994 | Huveteau et al. | |
| 5,664,447 | A * | 9/1997 | Neeley | E05B 13/101 70/178 |
| 5,771,924 | A * | 6/1998 | Huygen | F16K 17/168 251/335.2 |
| 5,924,443 | A * | 7/1999 | Wohlfahrt | G05D 16/0669 137/116.5 |
| 6,029,766 | A * | 2/2000 | Limberg | B62D 5/062 180/441 |
| 6,102,171 | A * | 8/2000 | Rottenberger | F16F 9/325 137/512.1 |
| 6,347,784 | B1 * | 2/2002 | Philipps-Liebich | F16K 31/60 251/109 |
| 2002/0100478 | A1 * | 8/2002 | Prime | A61M 16/109 128/203.14 |
| 2002/0104569 | A1 | 8/2002 | Massengale et al. | |
| 2005/0217731 | A1 * | 10/2005 | Abe | F16K 17/06 137/540 |
| 2010/0206310 | A1 | 8/2010 | Matsubara et al. | |
| 2011/0168180 | A1 | 7/2011 | Lugtigheid | |
| 2015/0083242 | A1 * | 3/2015 | Hirai | F16K 27/0209 137/540 |
| 2015/0362089 | A1 | 12/2015 | Fukushima | |
| 2022/0325811 | A1 * | 10/2022 | Tütek | F16K 27/02 |

FOREIGN PATENT DOCUMENTS

GB 2382639 A 6/2003
WO 2014/129407 A1 8/2014

OTHER PUBLICATIONS

Great Britain Search Report for corresponding Great Britain Application No. 1909121.4 (dated Dec. 9, 2019).
Great Britain Search Report for corresponding Great Britain Application No. 1909121.4 (dated Jun. 8, 2020).

* cited by examiner

ADJUSTABLE VALVE

This application is a national stage application under 35 U.S.C. § 371 of PCT Application No. PCT/EP2020/067950, filed Jun. 25, 2020, which claims the priority benefit of Great Britain Patent Application No. 1909121.4, filed Jun. 25, 2019.

The present invention relates to adjustable flow control valves, for example to an Adjustable Pressure Limiting (APL) valve.

An APL valve (sometimes referred to as an expiratory valve, relief valve or spill valve) is a type of flow control valve used in anaesthesiology as part of a breathing system. It allows excess fresh gas flow and exhaled gases to leave the system while preventing ambient air from entering.

APL valves comprise a thin disc shaped sealing member, held in place against a valve seat by a spring. Very light springs are typically used, to ensure that the valve can be opened just by a patient's breathing at low pressures. However, the opening pressure of the spring-loaded valve member can be increased by rotating a part of the valve top to compress the spring. The APL valve thus provides an adjustable limit pressure at which the valve member will open. In some instances, the valve can be configured so that rotating the same part of the valve top in an opposite direction can entirely remove the spring force from the valve member so that the valve has an open configuration.

It is important to the intended operation of APL valves that their maximum limit pressure is accurate and known. When manufacturing an APL valve, the target for maximum limit pressure may be 60 cmH$_2$O, for example. However, this can be difficult to achieve reliably/repeatably. The spring force provided by springs, in particular light springs, can vary. This, together with other manufacturing tolerances, often means that some springs will need compressing more than others to achieve a setting as close to 60 cmH$_2$O as possible.

It may be tempting to use a slightly stronger spring than necessary in order to ensure that all valves are capable of achieving the target. However, this would undesirably increase the pressure needed to open the APL valve at the low end of its operating range, and if the maximum limit pressure of a valve is higher than indicated a valve may not open at all.

A need existed, therefore, for an improved APL valve allow greater accuracy in the setting of the maximum pressure the valve allows.

According to the present invention, there is provided an adjustable valve as defined in the appended claim 1.

In summary, the valve of the invention comprises a first valve cap that can be used to adjust the force applied to a valve member by a biasing element, and a second valve cap that can be engaged with the first valve cap to prevent further adjustment beyond a predetermined maximum desired limit. For example, the valve may comprise a first or inner cap that can be rotated to move down a thread on the valve body, increasing the force applied by a spring to a valve member. When the pressure is as close to a target value (for example 60 cmH$_2$O) as possible a second, outer, valve cap then fits over the first/inner valve cap. The valve caps engage so that they cannot be rotated relative to one another, and corresponding abutment features on the second/outer valve cap and valve body are aligned to abut one another and prevent any further rotation to further compress the spring and thus prevent the pressure being set any higher.

Valves are known where an inner cap can be rotated to adjust a threshold pressure as described and then locked in place by an outer cap fixed or locked onto the valve body. However, in these valves, once the threshold pressure is set at a predetermined level (for example at 60 cmH$_2$O) it cannot be changed/adjusted at all.

By instead fixing the second/outer cap to the first/inner cap rather than the valve body, the valve of the present invention allows the maximum pressure to be adjusted as necessary and fixed, for example by a stop or abutment member, while still allowing adjustment of the valve during use so that a lower pressure can be delivered when needed. The first/inner cap can still be turned away from the stop to reduce pressure down towards 0.

Typically, where a valve provides an adjustable operating pressure with a maximum pressure threshold, the maximum pressure threshold is fixed during manufacture of the device (eg through the positioning of a stop on the screw fitting). However, this does not allow for any adjustment or 'fine tuning' of the valve, and therefore relies on very high consistency of springs and other valve components to achieve a reliable and consistent threshold across a number of individual valves or batches.

By providing a valve where the maximum pressure is finally set post-manufacture, by including a second cap as discussed, differences in springs or slight variations in manufacturing tolerances can be accommodated and corrected so that a quoted threshold pressure can be ensured.

According to the present invention there is provided an adjustable valve as defined in the appended claim 1. Further optional features are recited in the associated dependent claims.

The adjustable valve comprises a valve body comprising a valve seat, a valve member movable relative to the valve seat, a first valve cap, a second valve cap, and a biasing element provided between the first valve cap and the valve member such that the first valve member is biased away from the first valve cap by a biasing force from the biasing element. The first valve cap is movable within a defined range of motion relative to the valve body such that movement of the first cap in a first direction increases the biasing force applied by the biasing element and the second valve cap is engageable with the first valve cap at a plurality of positions of the first valve cap within its defined range of motion to prevent movement of the first valve cap in said first direction beyond a selected one of said plurality of positions but to allow movement of the valve cap in a second direction, opposite to said first direction, within said defined range of motion.

The adjustable valve allows the final setting of a maximum, or minimum, limit pressure during assembly, while still providing pressure adjustment during use.

The second valve cap may comprise a first abutment stop and the valve body may comprise a second abutment stop. Abutment of the first and second abutment stops may prevent movement of the first valve cap in said first direction.

The first abutment stop and/or the second abutment stop may comprise a projection of material, for example from valve body and/or from the second valve cap.

The first and second abutment stops may be moved into contact during engagement of the second valve cap with the first valve cap. The contact may comprise side-by-side abutment of the first and second abutment stops.

The valve body may comprise a screw thread to provide the defined range of motion for the first valve cap, and the first direction of movement of the first valve cap may comprise clockwise rotation relative to the valve body.

The first valve cap and/or second valve may be configured to resist relative movement of the second valve cap relative to the first valve cap once the second valve cap is engaged with the first valve cap. For example, the first valve cap and second valve cap may be sized to engage with an interference fit and/or at least one of the first valve cap and second valve cap may comprise one or more engagement features, such as clips, to resist disengagement of the second valve cap from the first valve cap. The outer cap may, for example, clip onto the inner cap to prevent removal of the outer cap after assembly.

The first valve cap and second valve cap may comprise corresponding engagement features, for example ridges and groves or keys and splines, to prevent rotation of the second valve cap relative to the first valve cap.

The valve body or the first valve cap may comprise a plurality of detents to define the plurality of positions of the first valve cap as a series of defined adjustment steps. The plurality of detents may be provided by a textured or ridged surface on the valve body, for example on an interior surface of the valve body, to engage with a feature on the interior of the first valve cap. The plurality of detents may be evenly spaced.

Alternatively, stepless adjustment may be provided between the first valve cap and the valve body.

The biasing element of the valve may comprise a compression spring.

A breathing system is also provided comprising a fresh gas inlet, a first outlet connectable to a user interface, and an adjustable valve as defined above provided at a second outlet located between the fresh gas inlet and the first outlet. The breathing system may further comprise a reservoir bag.

The invention also provides a method of setting an adjustable valve as defined in the appended claim 16. Further optional features are recited in the associated dependent claims.

The method comprises the steps of rotating a threaded adjuster relative to a valve housing to set a desired valve opening pressure and subsequently engaging a locking cap with the threaded adjuster such that a part of the locking cap abuts a part of the valve housing to prevent rotation of the threaded adjuster in a first direction but to permit rotation of the threaded adjuster in a second, opposite, direction.

The first direction may be a clockwise direction and the second direction may be an anticlockwise direction.

Engaging the locking cap with the threaded adjuster may permanently secure the locking cap to the threaded adjuster.

The method may be applied to the adjustable valve as previously described.

Wherever practicable, any of the essential or preferable features defined in relation to any one aspect of the invention may be applied to any further aspect. Accordingly, the invention may comprise various alternative configurations of the features defined above.

Practicable embodiments of the present will now be described with reference to the accompanying drawings, of which:

Figure 1:
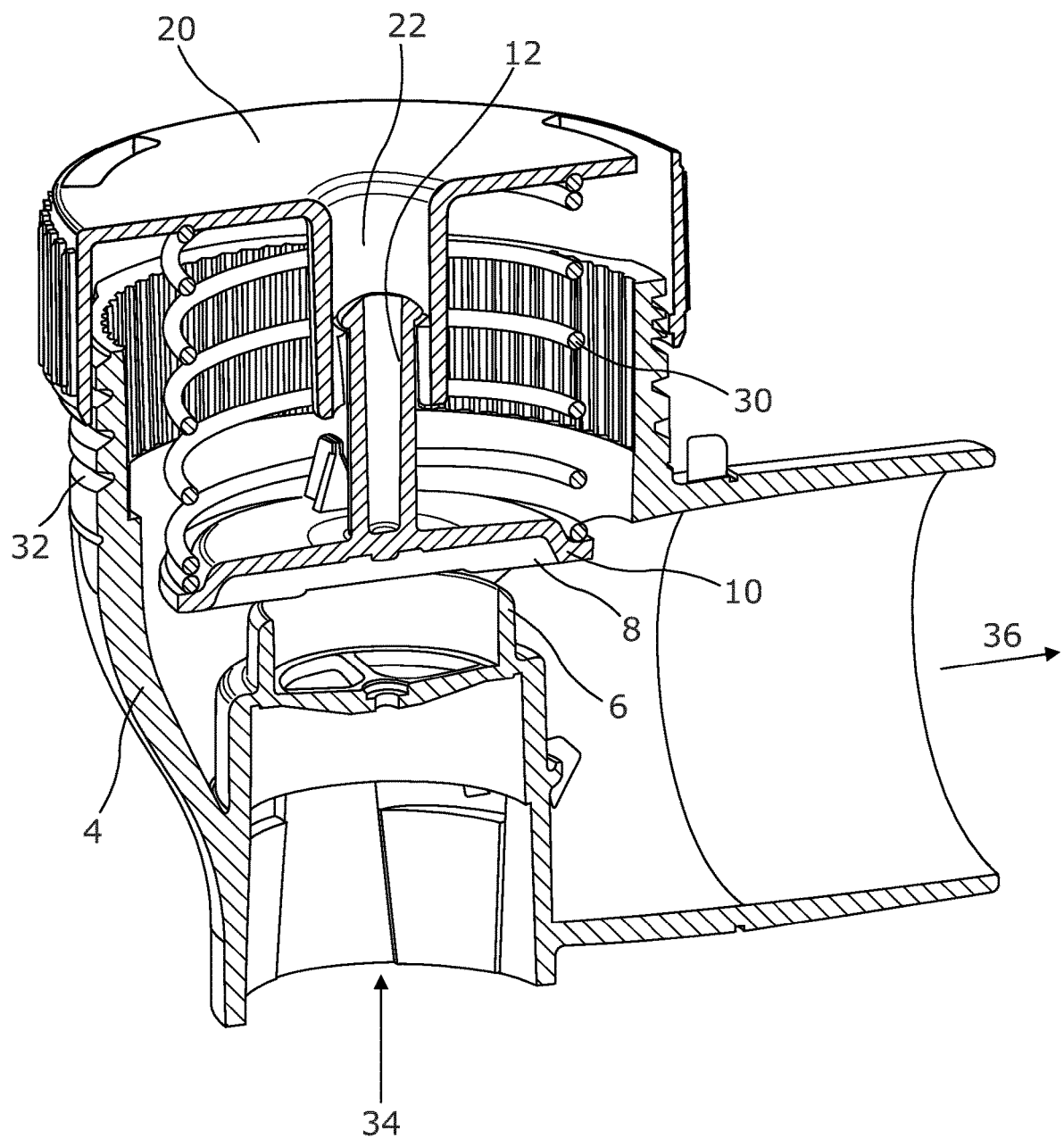
FIG. 1 is a cross-sectional perspective view of an incomplete APL valve according to the present invention.

A part assembled APL valve 2 is shown in FIG. 1. The valve 2 comprises a valve body 4 with an internally provided valve seat 6. The valve seat 6 is a generally cylindrical opening which can be closed by a generally circular disc shaped resilient element 8 on the lower side of a valve member 10. A generally tubular stem 12 extends from an upper side of the valve member 10 and is slidably received in a tubular opening 22 in a first valve cap 20. The movement of the valve member 10 is thus constrained by the cap 20 to vertical movement towards and away from the valve seat 6.

A coil spring 30 is provided between the cap 20 and valve member 10 to bias the valve member away from the cap 20. The cap 20 engages with a screw thread 32 on the exterior of the valve body 4, such that rotation of the cap 20 adjusts the vertical position of the cap 20 and valve member 10 relative to the valve seat 6. As illustrated in FIG. 1, the resilient element 8 of the valve member 10 is spaced from the valve seat 6 and the coil spring 30 is fully extended. It will be understood, however, that further movement of the cap 20 towards the valve seat once the resilient element 8 engages with the valve seat 6 will compress the coil spring 30 and thus increase the spring force applied to the valve member 10. This in turn allows a variation in the amount of pressure required to open the valve member 10 and allow gas flow from an inlet 34 to an outlet 36.

Figure 2:
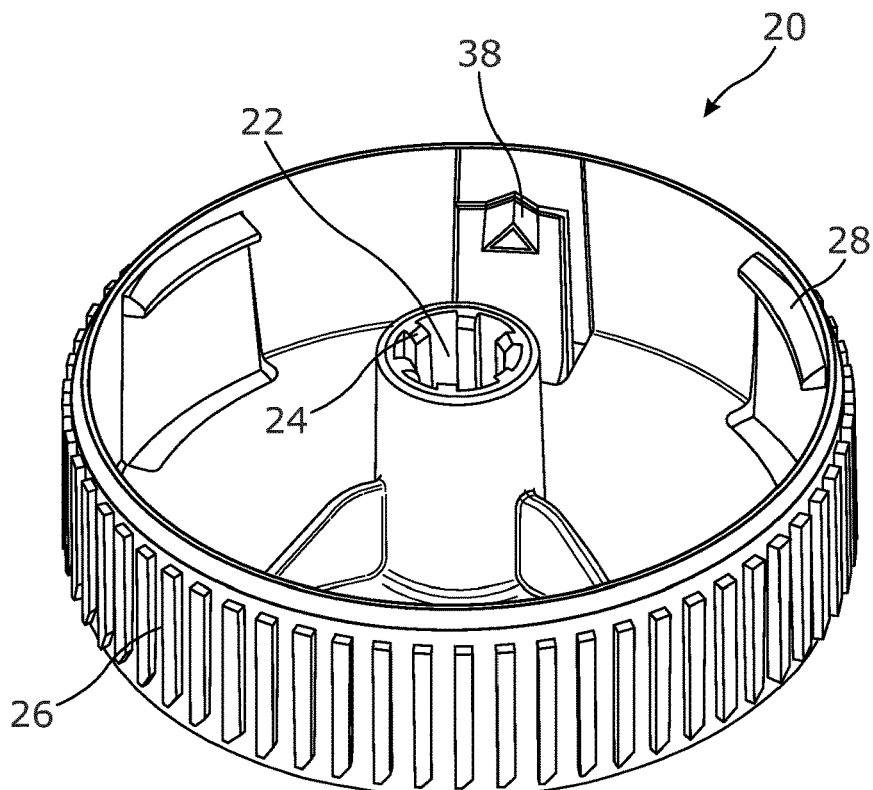
FIG. 2 is a perspective view of a first rotatable cap of the APL valve of FIG. 1.

The interior of the first valve cap 20 can be seen in FIG. 2. A set of support ridges 24 are provided within the tubular opening 22, and a set of external ridges 26 are provided around the exterior of the cap 20. Circumferential teeth or lugs 28, for engaging with the screw thread 32 on the valve body 4, can also be seen on an internal circumferential face of the cap 20. The lugs 26 clip into the screw thread 32 to hold the cap 20 on the valve body 4 and constrain rotation of the cap 20 within the screw thread 32 provided. A resiliently flexible ratchet tooth 38 is also shown facing radially outward towards this circumferential face.

Figure 3:
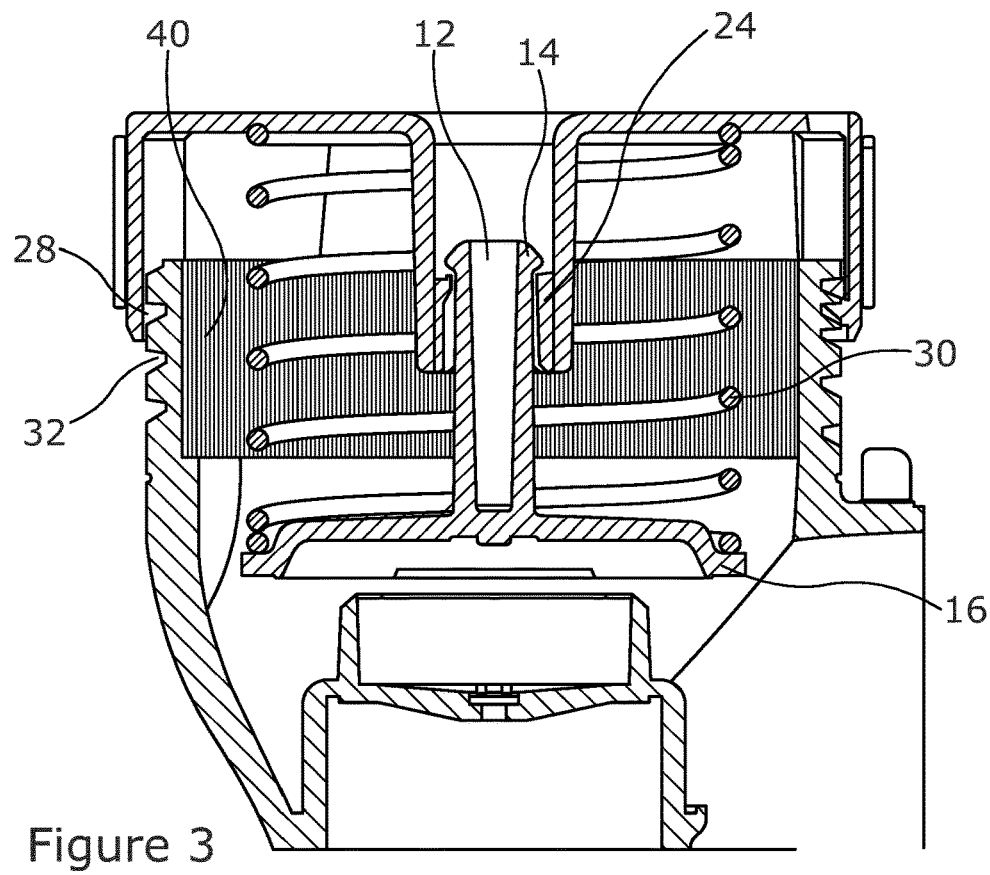
FIG. 3 is a cross-sectional view showing the internal components of the APL valve of FIG. 1.

The cross-sectional view of FIG. 3 shows the engagement of the circumferential teeth 28 of the cap 20 with the screw thread 32 on the valve body 4. An enlarged diameter portion 14 at a free end of the stem 12 of the valve member 10 is supported on the support ridges 24 of the cap 20. This helps to hold the valve member 10 against the biasing force of the coil spring 30, which is lightly compressed to ensure that it is seated and retained between the cap 20 and an annular rebate/stepped area 16 at the peripheral edge of the valve member 10. A textured/ridged surface 40 is also visible on the interior of the valve body. The radial tooth 38 of the cap 20 engages with this surface 40 to provide a stepped adjustment during rotation of the cap 20 relative to the valve body 4. This provides feedback during rotation and helps to maintain the cap 20 in a desired position, but the ridged surface 40 and/or radial tooth 38 could be omitted if finer, or stepless, adjustment is more desirable.

Figure 4A:
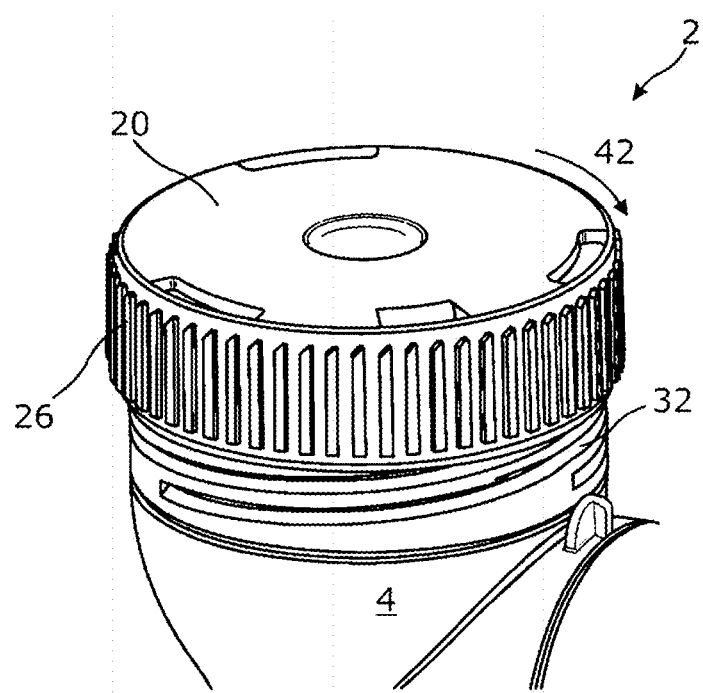
FIGS. 4A and 4B are perspective views showing adjustment of the APL valve of FIG. 1.
Figure 4B:
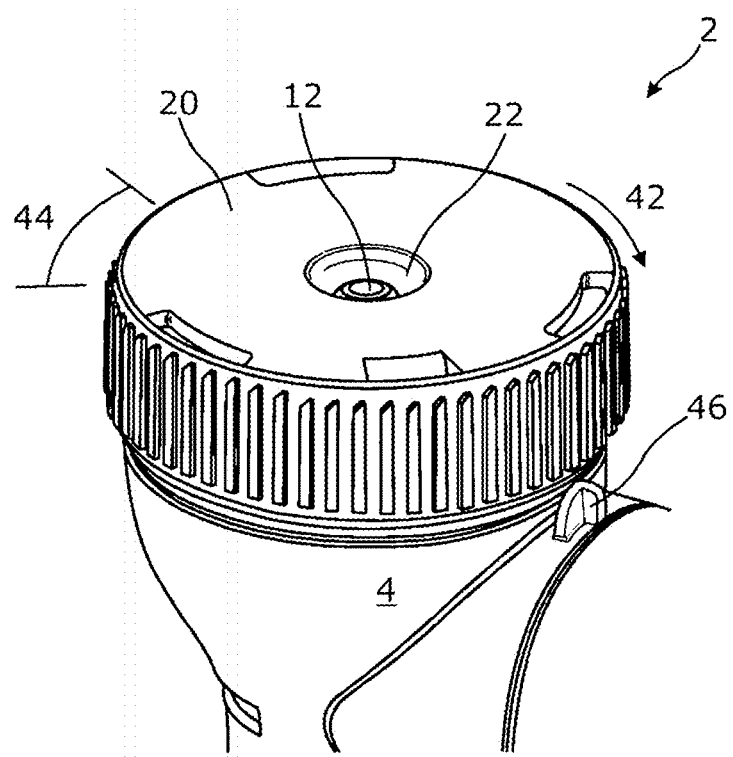

FIGS. 4A and 4B show the adjustment of the first valve cap 20 to set a desired threshold pressure for the valve 2. In FIG. 4A the first valve cap 20 is in a similar position to that shown in FIGS. 1 and 3. The majority of the screw thread 32 is visible, and inside the valve body 4 the resilient element 8 of the valve member 10 is spaced from the valve seat 6.

Clockwise rotation 42 of the first cap 20 will first move the valve member 10 towards the valve seat, and subsequently compress the coil spring 30 to increase the spring force provided to the valve member. During this adjustment, the valve 2 can be repeatably tested by applying a known gas pressure at the inlet 34 and monitoring gas flow at the outlet 36 of the valve 2.

FIG. 4B shows the same valve 2 adjusted to provide a threshold pressure set as close to 60 cmH$_2$O as possible. The cap has been rotated clockwise 42 from the position shown in FIG. 4A to screw the cap 20 down onto the valve body 4. The top of the stem 12 of the valve member 10 can be seen through the tubular opening 22 in the top of the first valve cap 20, forced upwards by the resilient element 8 of the valve member 10 engaging the valve seat 6 and compressing the spring 30 between the cap 20 and the valve member 10.

In an ideal world, the strength of the spring 30 and the area of the valve seat 6 in the illustrated example could simply be selected to provide a maximum threshold pressure of, for example, 60cmH$_2$O for the valve 2 when the cap 20 is fully tightened. However, in practice manufacturing tolerances in both the spring 30 and in the moulding of the valve seat 6 would lead to undesirable variations in threshold pressure between different valves 2, for example creating a threshold pressure of anywhere between 50 and 60 cmH$_2$O.

To help avoid producing a valve that provides too low a threshold pressure, elements of the valve 2 can be designed to provide a higher threshold pressure than required, for example 70 cmH$_2$O when fully tightened, so that natural manufacturing variations should provide a threshold pressure of 60 to 70 cmH$_2$O.

The higher threshold pressure can then be reduced, if necessary, during final assembly of the valve 2 by simply not fully tightening the first valve cap 20. For example, the valve shown in FIG. 4B has been adjusted so that the cap 20 is approximately 45 degrees 44 from being fully tightened, which equates to about 8 cmH$_2$O. This position has been determined to provide a threshold pressure as close as possible to 60 cmH$_2$O for the particular combination of components in the valve 2.

Once a desired threshold pressure is set, it is clearly important to prevent further rotation of the first valve cap 20 in the clockwise direction 42. This is achieved through the engagement of a second valve cap, designed to fit over the first valve cap 20 and engage with a first abutment stop 46 provided on the valve body 4.

Figure 5A:
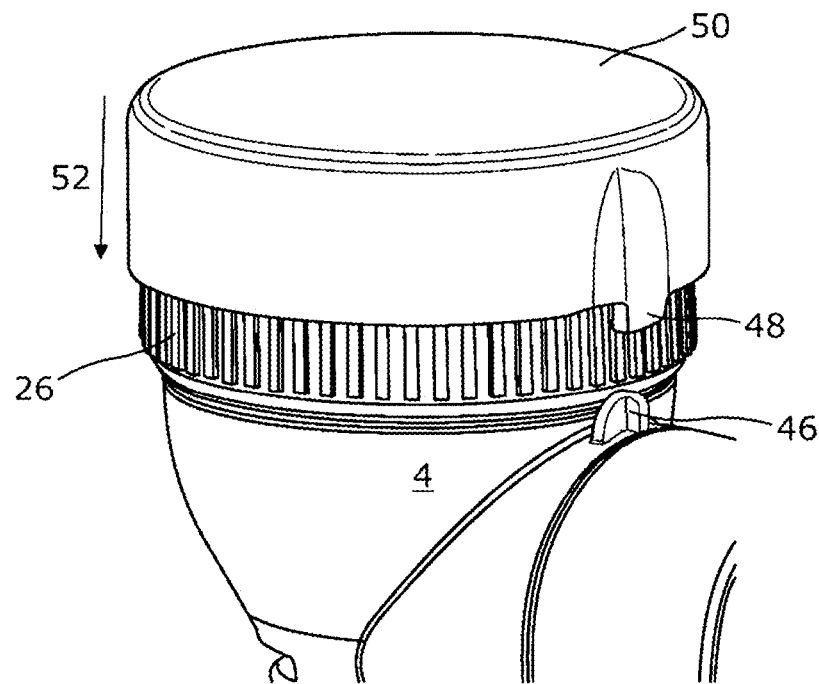
FIGS. 5A and 5B are perspective views showing the APL valve of FIG. 1 with a second rotatable cap for setting a threshold pressure.
Figure 5B:
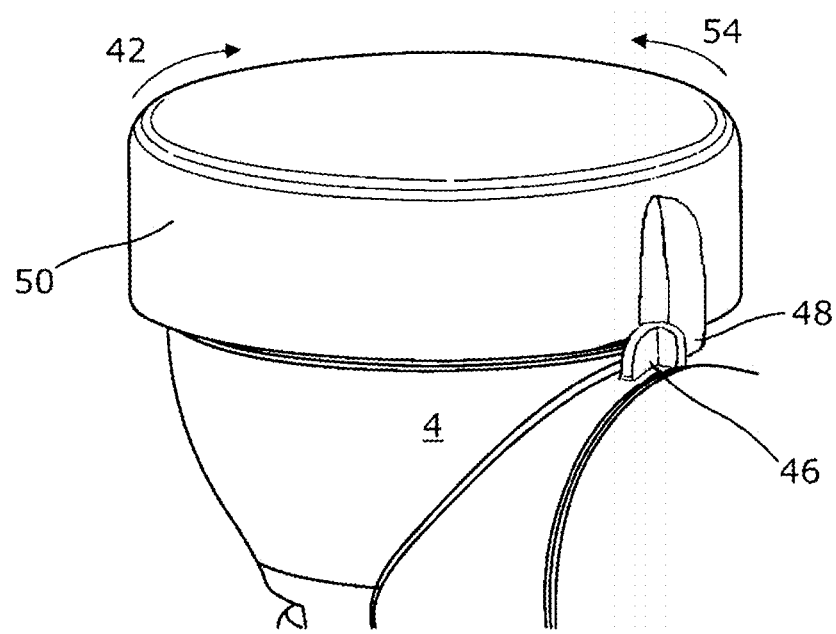

FIGS. 5A and 5B shown the fitting of the second valve cap 50. A projection 48 on the second valve cap 50 provides a second abutment stop 48 for engagement with the first abutment stop 46 on the valve body 4. Recesses (not shown) are provided on the interior of the second cap 50 to engage with the ridges 26 on the exterior surface first valve cap 20 as the second valve cap 50 is pushed down 52 into place. This provides a key and spline engagement to prevent relative rotation of the first and second valve caps 20,50.

The second valve cap 50 is assembled onto the first valve cap 20 such that the second abutment stop 48 on the second valve cap 50 abuts the first abutment stop 46 on the valve body, as shown in FIG. 5B. The ridges provided on the textured interior surface 40 of the valve body 4 correspond with the external ridges 26 on the outer periphery of the cap 20. The predefined adjustment steps provided by the ratchet tooth 38 engaging with the textured surface 40 therefore ensure that the second, or outer, valve cap 50 can be fitted in position with the first and second abutment stops 46,48 in contact without changing the rotational position of the first valve cap 20.

Once assembled as shown in FIG. 5B, the first and second valve caps 20,50 are prevented from rotating relative to one another, and the engagement of the first and second abutment stops 46,48 prevents rotation of the second valve cap 50 in the clockwise direction 42. The valve 2 therefore prevents an increase of threshold pressure beyond the desired level, such as 60 cmH$_2$O. The engagement of the first and second abutment stops 46,48 does not impede rotation of the first and second valve caps 20,50 in the anticlockwise direction 54, so the threshold pressure of the valve 2 can be adjusted to lower than 60 cmH$_2$O if required. Once the valve caps 20,50 are rotated anticlockwise 54 to the end of the screw thread 32, the valve member 10 will still be clear of the valve seat 6, as shown in FIGS. 1 and 3, so the valve 2 can still be set to a minimum threshold pressure of 0 cmH$_2$O if required. The threshold pressure at the fully open position of the valve 2 will thus always be 0 cmH$_2$O, regardless of the spring strength selected.

Figure 6:
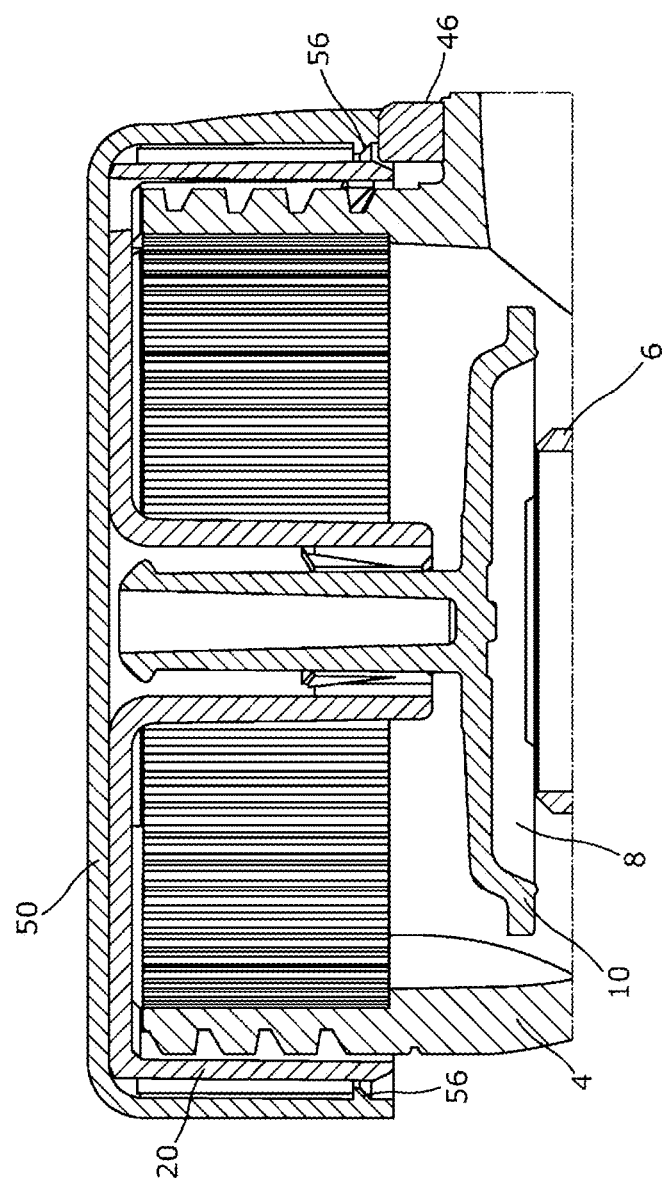
FIG. 6 is a cross-sectional view of the top of a complete APL valve as shown in FIG. 5B.

The outer/second valve cap 50 clips over the first valve cap 20 and locks these together so that once pushed down 52 into place during assembly, the second valve cap 50 cannot be readily removed from the first valve cap 20. FIG. 6 shows a cross-section of the arrangement. One or more clips 56 are provided around the periphery on the interior surface of the second valve cap 50, and engage underneath the ridges 26 on the outer surface of the first valve cap 20 to secure the caps 20,50 together. The valve member 10 can be seen within the valve body 4 in FIG. 6, with the resilient element 8 engaged with the valve seat 6. The coil spring 30 is omitted, and the second abutment stop 48 of the second valve cap 50 is obscured behind the first abutment stop 46 on the valve body 4.

Figure 7:
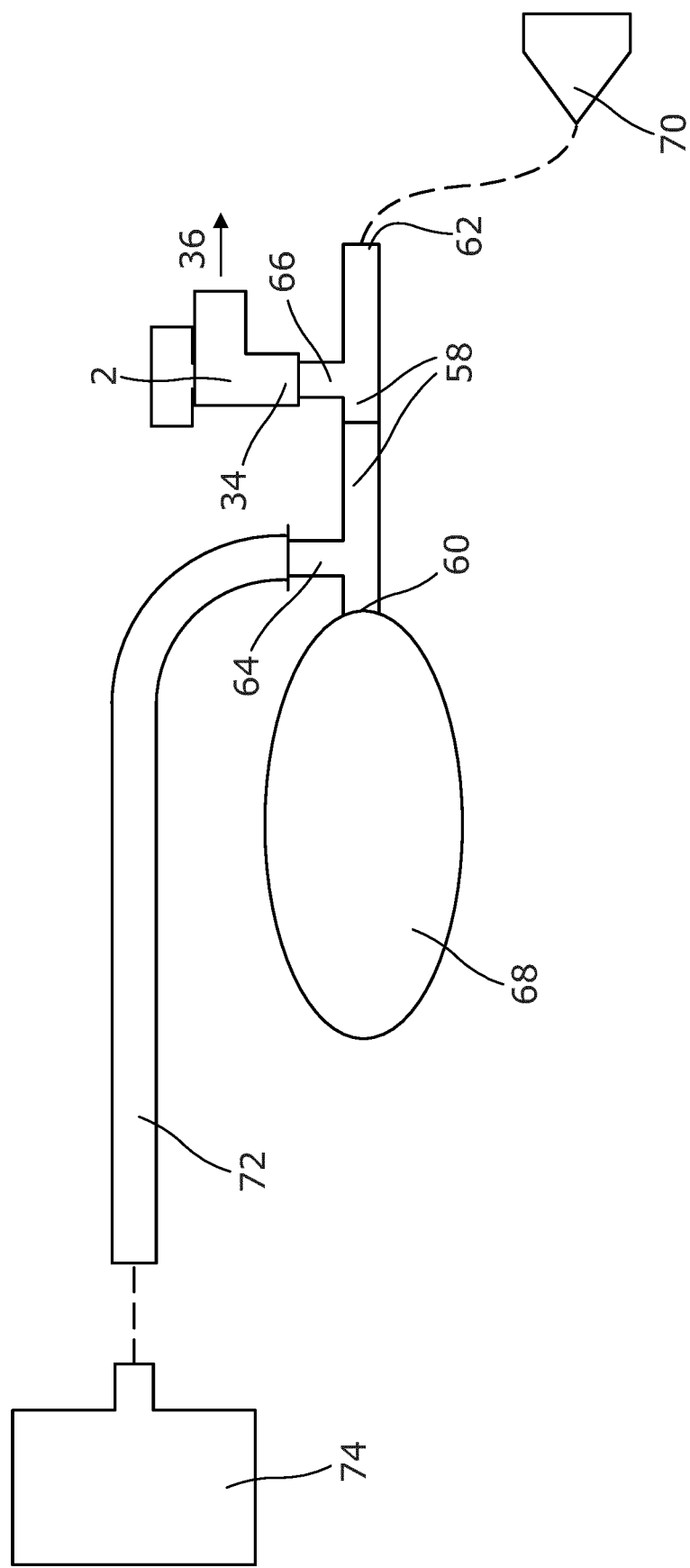
FIG. 7 is a schematic view of a breathing system incorporating an APL valve according to the present invention.

The breathing system of FIG. 7 includes a pair of T shaped connectors 58 providing a flow passageway with first and second ends 60,62 and first and second side connectors 64,66. It will be appreciated that a similar arrangement could be provided in a single, more complex, connecter piece if desired. The first end 60 is connected to a reservoir bag 68, while the second end 62 is connectable to a patient/user interface device 70, for example a breathing mask. The first side connector 64 is connected to a tube 72, which is in fluid connection with a fresh gas supply, for example an oxygen concentrator or other compressed gas source 74, a ventilator or an anaesthetic/anaesthesia machine.

The inlet 34 of the APL valve 2 of the invention is connected to the second side connector 66 to provide a pressure release valve. In the event that pressure within the system, for example on exhalation by a user, exceeds the pre-set valve for the APL valve 2, the valve member 10 will open and allow excess gas flow to pass through the valve 10 and out of the outlet 36.

Although described with reference to an APL valve, it should be noted that the design considerations and features described above could also be applied to similar valves which are capable of adjustment during use, for example adjustable Positive End Expiratory Pressure (PEEP) valves etc. It should also be understood that the threshold pressures discussed are included merely by way of example, and that appropriate design and selection of valve components could provide different maximum threshold pressures as required for a particular implementation.

The invention claimed is:

1. An adjustable valve comprising: a valve body comprising a valve seat; a valve member movable relative to the valve seat; a first valve cap; a second valve cap; and a biasing element provided between the first valve cap and the valve member such that the first valve member is biased away from the first valve cap by a biasing force from the biasing element; wherein the first valve cap is movable within a defined range of motion relative to the valve body such that movement of the first cap in a first direction increases the biasing force applied by the biasing element; and wherein the second valve cap is engageable with the first valve cap to prevent movement of the first valve cap in said first direction but to allow movement of the first valve cap in a second direction, opposite to said first direction, within said defined range of motion.

2. The adjustable valve according to claim 1, wherein the second valve cap comprises a first abutment stop and the valve body comprises a second abutment stop, and wherein abutment of the first and second abutment stops prevents movement of the first valve cap in said first direction.

3. The adjustable valve according to claim 2, wherein the first abutment stop and/or the second abutment stop comprises a projection of material.

4. The adjustable valve according to claim 2, wherein the first and second abutment stops are moved into contact during engagement of the second valve cap with the first valve cap.

5. The adjustable valve according to claim 1, wherein the valve body comprises a screw thread to provide the defined range of motion for the first valve cap.

6. The adjustable valve according to claim 5, wherein said first direction of movement of the first valve cap comprises clockwise rotation relative to the valve body.

7. The adjustable valve according to claim 1, wherein the first valve cap and/or second valve cap are configured to resist relative movement of the second valve cap relative to the first valve cap once the second valve cap is engaged with the first valve cap.

8. The adjustable valve according to claim 7, wherein the first valve cap and second valve cap are sized to engage one another with an interference fit.

9. The adjustable valve according to claim 7, wherein at least one of the first valve cap and second valve cap comprises one or more engagement features to resist disengagement of the second valve cap from the first valve cap.

10. The adjustable valve according to claim 7, wherein the first valve cap and second valve cap comprise corresponding engagement features to prevent rotation of the second valve cap relative to the first valve cap.

11. The adjustable valve according to claim 1, wherein the valve body or the first valve cap comprises a plurality of detents to define the plurality of positions of the first valve cap.

12. The adjustable valve according to claim 11, wherein the plurality of detents are provided by a textured or ridged surface on the valve body.

13. The adjustable valve according to claim 1, wherein the biasing element comprises a compression spring.

14. A breathing system comprising a fresh gas inlet, a first outlet connectable to a user interface, and an adjustable valve according to claim 1, wherein the adjustable valve is provided at a second outlet located between the fresh gas inlet and the first outlet.

15. The breathing system according to claim 14, further comprising a reservoir bag.

16. A method of setting an adjustable valve, comprising:
rotating a threaded adjuster relative to a valve housing to set a desired valve opening pressure and subsequently engaging a locking cap with the threaded adjuster such that a part of the locking cap abuts a part of the valve housing to prevent rotation of the threaded adjuster in a first direction beyond a point corresponding to the desired valve opening pressure but to permit rotation of the threaded adjuster in a second, opposite, direction.

17. The method according to claim 16, wherein the first direction is a clockwise direction and the second direction is a counter clockwise direction.

18. The method according to claim 16, wherein engaging the locking cap with the threaded adjuster permanently secures the locking cap to the threaded adjuster.

19. The method according to claim 16, wherein the adjustable valve comprises: a valve body comprising a valve seat; a valve member movable relative to the valve seat; a first valve cap; a second valve cap; and a biasing element provided between the first valve cap and the valve member such that the first valve member is biased away from the first valve cap by a biasing force from the biasing element; wherein the first valve cap is movable within a defined range of motion relative to the valve body such that movement of the first cap in a first direction increases the biasing force applied by the biasing element; and wherein the second valve cap is engageable with the first valve cap at a plurality of positions of the first valve cap within the first valve cap's defined range of motion to prevent movement of the first valve cap in said first direction beyond a selected one of said plurality of positions but to allow movement of the first valve cap in a second direction, opposite to said first direction, within said defined range of motion.

* * * * *